United States Patent [19]

Pestka et al.

[11] Patent Number: 5,633,157
[45] Date of Patent: May 27, 1997

[54] SIMPLE AND EFFICIENT METHOD FOR SITE-DIRECTED MUTAGENEIS WITH DOUBLE-STRANDED PLASMID DNA

[75] Inventors: Sidney Pestka, North Caldwell; Derhsing Lai, East Brunswick; Xueli Zhu, Iselin, all of N.J.

[73] Assignee: University of Medicine & Dentistry of New Jersey, Newark, N.J.

[21] Appl. No.: 601,698

[22] Filed: Feb. 15, 1996

Related U.S. Application Data

[63] Continuation of Ser. No. 503,787, Jul. 18, 1995, abandoned, which is a continuation of Ser. No. 145,329, Oct. 29, 1993, abandoned.

[51] Int. Cl.$^6$ .............................. C12N 15/09; C12N 15/01
[52] U.S. Cl. ......................... 435/172.3; 435/172.1
[58] Field of Search .......................... 435/172.3, 320.1, 435/172.1; 536/23.1

[56] References Cited

PUBLICATIONS

Hofer et. al. (1989) Gene 84, 153–157.
Inouye et. al. (1987), in "Synthesis & Applications of DNA & RNA", ed. Narang, pp. 181–206, Academic Pr.
Morinaba et. al. (1984), Bio/Technol. 2, 636–639.
Slilaty et. al. (1990) Anal. Biochem. 185, 194–200.

*Primary Examiner*—George C. Elliott
*Attorney, Agent, or Firm*—Richard R. Muccino

[57] ABSTRACT

This invention relates to a method for preparing site-specific mutations in double-stranded plasmid DNA which comprises the steps of (a) double digesting a plasmid having a site A, which contains a target sequence, and sites B and C, which flank site A, with restriction endonucleases A and B to produce fragment I and with restriction endonucleases A and C to produce fragment II, wherein restriction endonuclease A produces a 3' or 5' overhang; (b) denaturing fragments I and II to form a mixture; (c) reannealing the mixture from step (b) to produce parental homoduplex fragments I and II, heteroduplex fragment III, and heteroduplex fragment IV; (d) extending the 3' ends of the heteroduplex fragments; and (e) ligating the heteroduplex fragments to produce the double-stranded plasmid DNA mutant.

6 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

CAAGCTTATC GATACCGTCG 20

SIMPLE AND EFFICIENT METHOD FOR SITE-DIRECTED MUTAGENEIS WITH DOUBLE-STRANDED PLASMID DNA

This is a continuation application of patent application Ser. No. 08/503,787, filed 18 Jul. 1995, which application is a continuation of application Ser. No. 08/145,329, filed 29 Oct. 1993, both now abandoned.

FIELD OF THE INVENTION

The present invention is directed at a general, simple and efficient method for preparing site-specific mutations in double-stranded plasmid DNA without the need for special plasmids, bacterial strains, or reagents. Only one synthetic oligonucleotide primer for each mutation is required and subcloning is unnecessary.

BACKGROUND OF THE INVENTION

The disclosures referred to herein to illustrate the background of the invention and to provide additional detail with respect to its practice are incorporated herein by reference and, for convenience, are numerically referenced in the following text and respectively grouped in the appended bibliography.

Oligonucleotide-directed site-specific mutagenesis is a powerful method that is commonly used to create desired mutations. Three basic methods have been used for this purpose: the use of single-stranded (M13),[1,2] the polymerase chain reaction (PCR),[3-6] and the double-stranded plasmid method.[7-9] The single-stranded method originally developed by Zoller and Smith has been used for years.[10] Many modifications have been made to achieve a higher yield of mutants. The PCR method also has become another popular technique for site-directed mutagenesis. The advantages and shortcomings of these methods have been discussed.[11,12] Briefly, limitations include the availability of restriction sites for subcloning and the instability of large insertions (larger than 2 kilobases) in M13 vectors,[13] the low fidelity of the Taq polymerase and the expense for multiple primers in the PCR methods, and the low mutant yields with the double-stranded plasmid method.

SUMMARY OF THE INVENTION

Figure 1:
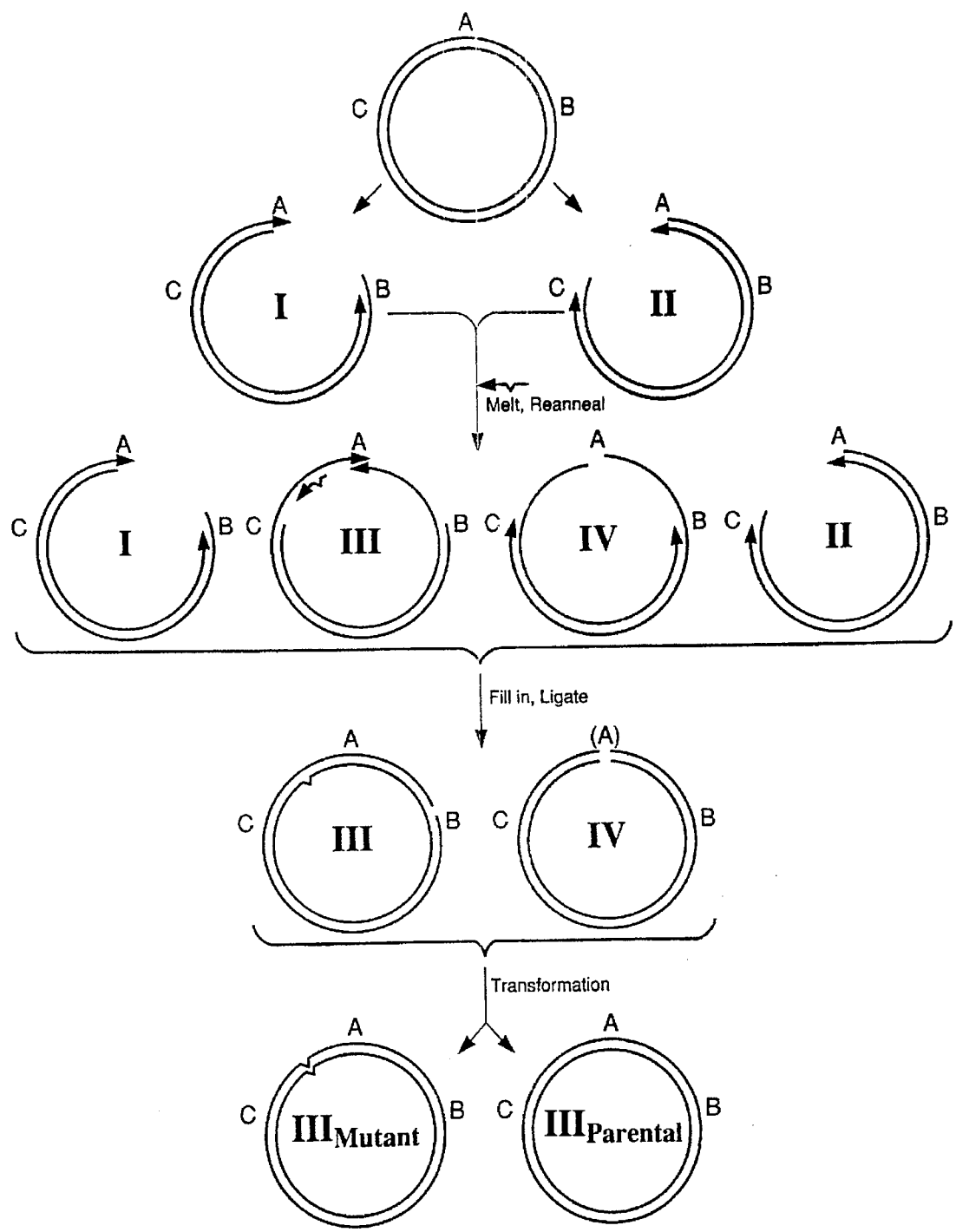
FIG. 1 is a diagram of the strategy of the double-stranded DNA site-specific method with restriction endonuclease A producing a 3' overhang.

This invention relates to a method for preparing site-specific mutations in double-stranded plasmid DNA which comprises the steps of:

(a) double digesting a plasmid having a site A, which contains a target sequence, and sites B and C, which flank site A, with restriction endonucleases A and B to produce fragment I and with restriction endonucleases A and C to produce fragment II, wherein restriction endonuclease A produces a 3' overhang;

(b) denaturating fragments I and II to form a mixture;

(c) reannealing the mixture from step (b) to produce parental homoduplex fragments I and II having a 3'-overhang and a 5'-overhang, heteroduplex fragment III, and heteroduplex fragment IV;

(d) extending the 3' ends of heteroduplex fragment III; and (e) ligating heteroduplex fragment III to produce the double-stranded plasmid DNA mutant.

This invention also relates to a method for preparing site-specific mutations in double-stranded plasmid DNA which comprises the steps of:

(a) double digesting a plasmid having a site A, which contains a target sequence, and sites B and C, which flank site A, with restriction endonucleases A and B to produce fragment I and with restriction endonucleases A and C to produce fragment II, wherein restriction endonuclease A produces a 5' overhang;

(b) denaturating fragments I and II to form a mixture;

(c) reannealing the mixture from step (b) to produce parental homoduplex fragments I and II having a 5'-overhang and a 3'-overhang, heteroduplex fragment III, and heteroduplex fragment IV;

(d) extending the 3' ends of heteroduplex fragment IV; and (e) ligating heteroduplex fragment IV to produce the double-stranded plasmid DNA mutant.

DETAILED DESCRIPTION OF THE INVENTION

The present invention is directed at a general, simple and efficient method for preparing site-specific mutations in double-stranded plasmid DNA without the need for special plasmids, bacterial strains, or reagents. No special *Escherichia coli* mutant strains, unusual nucleotides or specific modification enzymes are required. In the present method, only one synthetic oligonucleotide primer for each mutation is required and subcloning is unnecessary. A high efficiency of mutation (45–100%) is obtained. The entire procedure can be completed easily within a few days. If two synthetic oligonucleotide primers are used, one can create two separate mutations at the same time in a single reaction tube. A white/blue assay with the "BLUESCRIPT" k/s II vector was used to calculate the efficiency of this method. The novel method may be used to generate base changes, insertions, and deletions in the target DNA.

The present invention is further illustrated by the following examples which are not intended to limit the effective scope of the claims. All parts and percentages in the examples and throughout the specification and claims are by weight of the final composition unless otherwise specified.

EXPERIMENTAL PROCEDURES

Vector and Cells

The "BLUESCRIPT" k/s II vector (Stratagene) was modified by cutting the ClaI site within the polylinker, blunting the ends with the Klenow fragment of DNA polymerase I, and religating to yield plasmid pDL1. This eliminated the ClaI site and introduced a frameshift (two additional bases: CG) into the coding sequence for the lac α-peptide, resulting in a white colony phenotype on indicator plates. Competent cells were prepared by the procedure of Nishimura et al.[14] *Escherichia coli* DH5α and JM109 were used to prepare competant cells.

The Synthetic Primer (5'-CAAGCTTATCGATACCGTCG-3') (SEQ ID NO: 1)

This primer (I) was used to reconstruct the ClaI site in the lac Z gene by deletion of the two extra bases (CG) and produces the wild type lac α-peptide sequence which in turn restores the blue colony phenotype.

The Mutagenesis Method

The experimental procedure is a modification of that reported by Inouye et al.[12] The procedure is outlined in FIG. 1. The experimental vector pDL1 was double-digested with restriction endonucleases XbaI (B), PstI (A) to produce fragment I and with XhoI (C), PstI (A) to produce fragment II. After digestion with enzymes A and B to produce fragment I, this reaction mixture only was further treated with calf-intestinal alkaline phosphatase to remove 5'-phosphate termini where noted. Gel electrophoresis (1% agarose; TAE buffer, 0.04M Tris•acetate, 0.001M EDTA, pH 7.6; 94 volts; 45 min.) was used to isolate the fragments and "GENECLEAN" (Bio101) used to recover fragments I and II. The synthetic oligonucleotide primer (I) was incubated with T4 DNA kinase to phosphorylate the 5'-end of the primer.

Equimolar amounts (0.3–0.4 µg) of DNA fragments I and II were mixed with a 500-fold or 2000-fold molar excess of synthetic phosphorylated oligonucleotide primer as noted. The control groups contained no primer. The reaction mixture contained 172 mM NaCl, 12 mM Tris/HCl (pH 7.5), 14 mM $MgCl_2$, 1.7 mM 2-mercaptoethanol in a final volume of 35 µl. The mixture was incubated in boiling water for 3 minutes to denature the DNA fragments. After denaturation, the mixture was transferred to 30° C. for 30 minutes, then to 4° C. for 30 minutes, and then for at least 10 minutes on ice to allow the denatured DNA fragments to reanneal. The formation of new heteroduplex DNAs was confirmed by 1% agarose gel electrophoresis in TAE buffer before proceeding to the next step. To extend the 3'-ends and ligate the resulting heteroduplex plasmid (III, FIG. 1), 11.6 µl of the above reaction mixture was incubated with 5 units of "SEQUENASE™" or the Klenow fragment of DNA polymerase I (0.4 µl), 2 µl of T4 DNA ligase (2 units), 4 µl 2.5 mM dNTPs, and 2 µl 10 mM ATP in a final volume of 20 µl at 15° C. overnight. After the reaction, 5 µl of the mixture was then used to transform competent bacteria and the mixture plated on a LB agar plate containing 100 µg/ml ampicillin. Prior to plating the bacteria, the surface of the plate was coated with 44 µl of a solution of 5-bromo-4-chloro-3-indolyl-β-D-galactoside (40 µl X-gal, 20 mg/ml) and isopropyl-β-D-thiogalactopyranoside (4 µl IPTG, 200 mg/ml) as reported (Sambrook et al.[15]). The ratio of blue to white colonies was used to calculate the mutation efficiency. Because transformation was performed with double-stranded DNA, each blue colony represents a 50% mixture of the wild type and mutant plasmids.

FIG. 1 is a diagram of the strategy of the double-stranded DNA site-specific method with restriction endonuclease A producing a 3' overhang. The plasmids are digested with restriction endonucleases A and B, and A and C to yield I and II, respectively. In this example, the A restriction endonuclease site produces a 3'-protruding end. The B and C sites can be any sites flanking the target sequence. After denaturation and renaturation, the four heteroduplexes (I, II, III, IV) are formed. The parental plasmids (I and II) and blunt end ligated plasmid (IV) will yield no transformants. Only heteroduplex III can be extended and efficiently ligated. The A in parentheses means the site may no longer be intact. The theoretical mutation percentage is 50%. In the example shown in the text and in Tables 1 and 2, the restriction endonucleases are represented as follows: A, PstI; B, XbaI; and C, XhoI. Arrowheads in the top half of the figure represent the 3' ends of the DNA strands.

Figure 2:
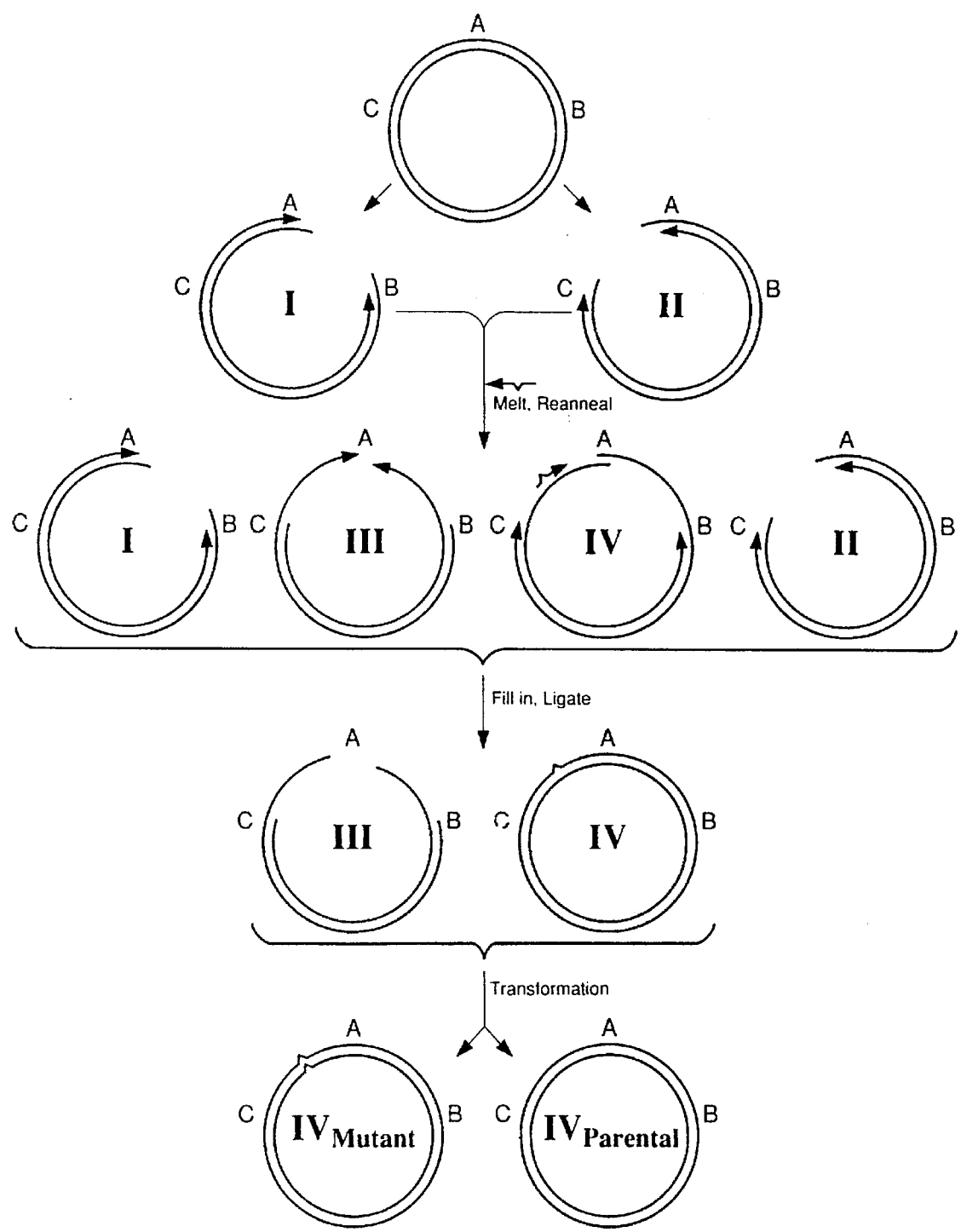
FIG. 2 is a diagram of the strategy of the double-stranded DNA site-specific method with restriction endonuclease A producing a 5' overhang.

FIG. 2 is a diagram of the strategy of the double-stranded DNA site-specific method with restriction endonuclease A producing a 5' overhang. If restriction endonuclease A is chosen to be one that produces a 5' overhang, then the mutation oligonucleotide must be complementary to the opposite strand as that shown in heteroduplex III of FIG. 1 and only heteroduplex IV produces a functional closed single-stranded circle after ligation.

Figure 3:
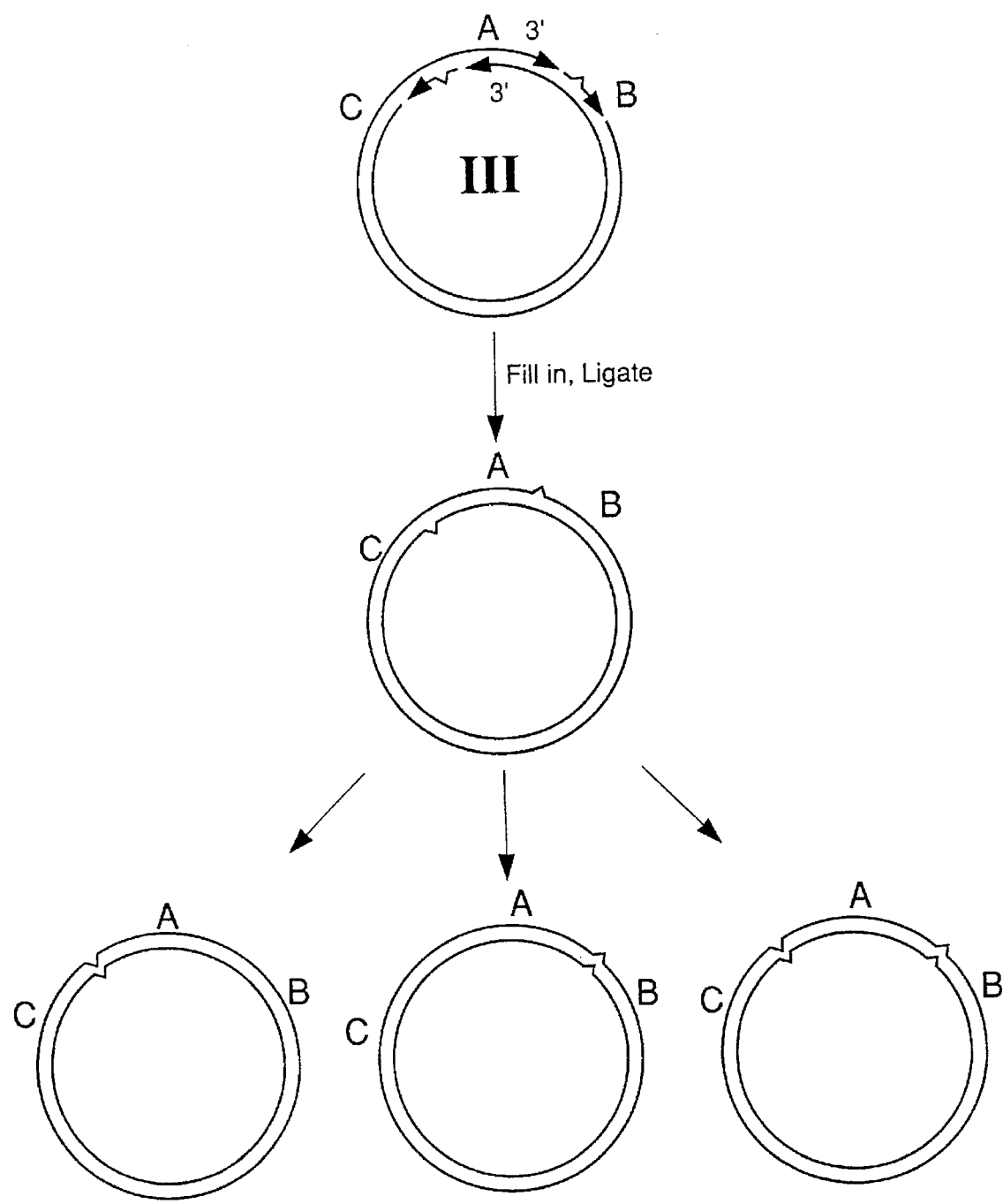
FIG. 3 is a diagram of the strategy with two synthetic primers.

FIG. 3 is a diagram of the strategy with two synthetic primers. This represents a variation of the procedure shown in FIG. 1 with the use of two oligonucleotide primers to produce two single and one double mutation simultaneously. Dephosphorylation of Fragment I (FIG. 1) is unnecessary.

TABLE 1

| Mutation Rate with Double-Stranded DNA | | | | | | | |
|---|---|---|---|---|---|---|---|
| | Experiment | | | | | | |
| Group | 1 | 2 | 3 | 4 | 5 | 6 | 7 |
| Alkaline Phosphatase | No | No | No | Yes | Yes | Yes | Yes |
| Blue Colony | 41 | 71 | 26 | 16 | 20 | 17 | 89 |
| White Colony | 25 | 42 | 32 | 2 | 1 | 0 | 3 |
| Blue/Total (%) | 62 | 62 | 45 | 88 | 95 | 100 | 96 |

The experiments 1–4 were performed as described in Experimental Procedures except as noted. Briefly, an equal amount of both pDL1 XboI, PstI-treated fragment II and XbaI, PstI treated fragment I were incubated with a 500-fold excess of phosphorylated primer I. The reaction was boiled in water for 3 minutes and then transferred to a 30° C. water bath for 30 minutes, then transferred to 4° C. for another 30 minutes. As described under "Experimental Procedures" four µl of 2.5 mM dNTP, 2 µl of 10 mM ATP, 0.4 µl of the Klenow fragment of DNA Polymease I (5 units) and 2 µl of T4 DNA ligase (2 units) were added to the 11.6 µl of sample from the above reaction and incubated at 15° C. overnight. After overnight incubation, the mixture was used to transform *E. coli* DH5α competent bacteria and the mixture plated on a LB agar plate containing 100 µg/ml ampicillin, X-gal and IPTG as described. The ratio of blue to white colonies was used to calculate the mutation efficiency. DNA from the blue colonies was checked by restriction endonuclease ClaI digestion. Experiment 4 was performed as experiments 1–3 except that the pDL1 (XbaI, PstI) fragment (A-B fragment I, FIG. 1) was treated with alkaline phosphatase after the restriction enzyme digestion. Experiments 5–7 were performed as experiments 1–3 with minor modifications: the pDL1 XbaI, PstI fragment (A-B fragment I, FIG. 1) was treated with alkaline phosphatase after the restriction enzyme digestion; *E. coli* JM109 competent cells and 2000-fold excess of phosphorylated primer I were used. White colonies represent wild type and blue colonies, mutants.

RESULTS AND DISCUSSION

As shown in Table 1, the mutation rate was 45 to 100% with the double-stranded DNA transformation. In this strategy (FIG. 1), restriction endonuclease A must have overhanging ends which are shared by the two double-digested fragments I and II. There are no constraints for the other restriction endonucleases B and C except that they need to produce fragments I and II. One or more B sites may be present in the gap produced by the A and B double digestion (FIG. 1); and similarly one or more C sites may be present in the gap produced by digestion with enzymes A and C (FIG. 1). After reannealing and 3'-extension, duplexes I and II cannot religate since they retain a 3'-overhang and a blunt end. When restriction endonuclease A produces a 3' overhang (e.g., PstI), Duplex IV produces a blunt-ended DNA that will not be religated significantly at the low concentrations of the ligase used. This was confirmed by demonstrating that blunt-ended heteroduplex DNA produced no colonies after transformation (data not shown). Duplex III, therefore, is the only one that can religate efficiently after 3'-extension. This design provides a theoretical mutation rate of 100%.

It should be noted that if restriction endonuclease A is chosen with a 5' overhang, then duplex III cannot be extended and filled in (FIG. 2). The oligonucleotide must be complementary to the opposite strand as that shown in FIG. 1 (heteroduplex III) so that heteroduplex IV is the only one that religates the outer strand (FIG. 2).

In practice, the mutant yield may be somewhat lower than the theoretical ratios although they approximated the theoretical values as shown in Table 1. This is assumed to be due to such factors as incomplete in vitro DNA polymerization, primer displacement by the DNA polymerase used to fill in the strands and primer phosphorylation efficiency. We did not use a repair minus *E. coli* strain (e.g., BMH 71-18 mutS)[16,17] in these experiments as our actual mutation rates were almost equivalent to the theoretical rates. This strain suppresses in vitro mismatch repair and was used to construct two mutants of the soluble receptor for murine interferon gamma (data not shown). However, the mutation rate was not significantly different between the bacterial strains. Thus, special strains are not critical for this method.

This mutation method has some advantages over others. Its efficiency is as high as that of the single-stranded method. The procedure is more consistent and rapid compared with the single-stranded method[1,2] because subcloning into a single-stranded vector or a vector with an M13 origin can be omitted. In addition, the cost for primer synthesis is less than the costs with PCR methods since only one primer is required. Furthermore, the procedure can be modified by using two primers to generate three mutants (two single mutants, one double mutant) in the same experiment (FIG. 3). We have routinely used this method to create mutants of the extracellular domain of the murine interferon gamma receptor, mutant #4740 (Lys$^{111}$/Ala), mutant #4741 (His$^{196}$/Ala) and mutant #4136 (Asp$^{118}$/Ala) with mutation rates of 5%, 3% and 10%, respectively.

If the reaction mixture is boiled for 3 minutes just prior to transformation, then only the ligated mutant strand survives as the other strand cannot be ligated. By transformation of *E. coli* competent cells with the resultant single-stranded DNA, only mutant strands should survive as all the parental strands will be linearized. Thus, transformation of the mixture after melting will produce mutants at 100% efficiency. This additional step avoids the need to screen colonies. Although transformation of single-stranded DNA is about one hundredth the efficiency of transformation with double-stranded plasmid DNA, the resultant library of transformants will eliminate the need to screen colonies.

This method can be used with plasmids containing three suitable restriction enzyme sites to generate base changes, deletions and insertions in the target DNA. The method is a general one that is convenient and rapid. Insertion and deletion mutants can be easily identified without the need for sequencing. In fact, single base changes can be identified rapidly by PCR by preparing an oligonucleotide with the mutant base at the 3'-end.[18,19] Because no specific plasmids or *E. coli* strains are required, the simplicity and high efficiency of this method should make it a useful general procedure for preparing site-specific mutations in double-stranded DNA.

Appendium of References

1. Derbyshire, K. M., Salvo, J. J., Grindley, N. D. F. (1986) A simple and efficient procedure for saturation mutagenesis using mixed oligodeoxy nucleotides. *Gene* 46, 145-152.
2. Li, B., Langer, J. A., Schwartz, B., and Pestka, S. (1989) Creation of phosphorylation sites in proteins: Construction of a phosphorylatable human interferon α. *Proc. Natl. Acad. Sci. USA* 86, 558-562.
3. Hignichi, R., Krummel, B., and Saiki, R. K. (1988) A general method of in vitro preparation and specific mutagenesis of DNA fragments: study of protein and DNA interactions. *Nucleic Acid Res.* 16, 7351-7367.
4. Vallette, F., Mege, E., Reiss, A., and Adesnik, M. (1989) Construction of mutant and chimeric genes using the polymerase chain reaction. *Nucleic Acid Res.* 17, 723-733.
5. Kadowaki, H., Kadowaki, T., Wondisford, F. E., and Taylor, S. I. (1989) Use of polymerase chain reaction catalyzed by Taq DNA polymerase for site-specific mutagenesis. *Gene* 76, 161-166.
6. Ho, S., Hunt, H. D., Horton, R. M., Pullen, J. K., and Pease, L. R. (1989) Site-directed mutagenesis by overlap extension using the polymerase chain reaction. *Gene* 77, 51-59.
7. Vlasuk, G. P., and Inouye, S. (1983) In: Experimental Manipulation of gene expression. (M. Inouye, ed)., pp. 291-303. Academic Press, New York.
8. Morinaga, Y., Franceschini, T., Inouye, S., and Inouye, M. (1984). Improvement of oligonucleotide-directed site-specific mutagenesis using double-stranded plasmid DNA. *Bio/Technology* 2, 636-639.
9. DeChiara, T. M., Erlitz, F., and Tarnowski, S. J., (1986) Procedures for in vitro DNA mutagenesis of human leukocyte interferon sequences. *Methods in Enzymology* 119, 403-415.
10. Zoller, M. J., and Smith, M. (1982) Oligonucleotide-directed mutagenesis using M3-derived vectors: an efficient and general procedure for the production of point mutations in any fragment. *Nucleic Acid Res.* 10, 6487-6500.
11. Jones, D. H., and Howard, B. H. (1990) A rapid method for site-specific mutagenesis and directional subcloning by using the polymerase chain reaction to generate recombinant circles. *BioTechniques* 8, 178-183.
12. Inouye, S. and Inouye M. (1987) Oligonucleotide-directed site-specific mutagenesis using double-stranded plasmid DNA. *Synthesis and Applications of DNA and RNA*, Academic Press, Inc.
13. Cordell, B., Bell, G., Tisher, E., DeNoto, F. M., Ullrich, A., Pictet, R., Rutter, W. J., and Goodman, N. M. (1979) Isolation and characterization of a cloned rat insulin gene. *Cell* 18, 533-543.
14. Nishimua, A., Morita, M., Nishimura, Y., and Sugino, Y. (1990) A rapid and highly efficient methods for preparation of competent *Escherichia coli* cells. *Nucleic acid Res.* 18, 6169.
15. Sambrook, J., Fritsch, E. F., and Maniatis, T. (1989) Molecular cloning, a laboratory manual, second edition, Cold Spring Harbor Laboratory Press, 3 volumes.
16. Kramer, B., Kramer, W., and Fritz, H. J. (1984) Different base/base mismatches are corrected with deficient efficiencies by the methyl-directed DNA mismatch-repair system of *E. coli*. *Cell* 38, 879-887.
17. Zell, R., and Fritz, H. J. (1987) DNA mismatch repair in *Escherichia coli* counteracting the hydrolytic deamination of 5-methyl-cytosine residues. *EMBO. J.* 6, 1809-1815.
18. Newton, C. R., Graham, A., Heptinstall, L. E., Powell, S. J., Summers, C., Kalsheker, N., Smith, J. C., and Markham, A. F. (1989) Analysis of any point mutation in DNA. The amplification refractory mutation system (ARMS). *Nucleic Acid Res.* 17, 2503-2515.
19. Sommer, S. S., Cassady, J. D., Sobell, J. L., and Bottema, C. D. K. (1989) A novel method for detecting point mutations or polymorphisms and its application to population screening for carriers of phenylketonuria. *Mayo Clin. Proc.* 64, 1361-1372.

The invention being thus described, it will be obvious that the same may be varied in many ways. Such variations are not to be regarded as a departure from the spirit and scope of the invention and all such modifications are intended to be included within the scope of the following claims.

We claim:

1. A method for preparing site-specific mutations in double-stranded plasmid DNA which comprises the steps of:
   (a) double digesting a plasmid having a restriction site A, which contains a target sequence, and restriction sites B and C, which flank restriction site A, with restriction endonucleases A and B to produce fragment I and with restriction endonucleases A and C to produce fragment II, wherein restriction endonuclease A produces a 3' overhang;
   (b) denaturating fragments I and II to form a mixture;
   (c) annealing the mixture from step (b) to produce parental homoduplex fragments I and II having a 3'-overhang and a 5'-overhang, heteroduplex fragment III, and heteroduplex fragment IV;
   (d) providing an oligonucleotide primer that can hybridize with the single-stranded region of the heteroduplex fragment III and that has a sequence that directs mutagenesis;
   (e) extending the 3' ends of heteroduplex fragment III; and
   (f) ligating heteroduplex fragment III to produce the double-stranded plasmid DNA mutant.

2. The method according to claim 1, wherein fragment I is dephosphorylated at the 5' terminii prior to step (b).

3. The method according to claim 1, wherein two oligonucleotide primers are ligated to different strands.

4. A method for preparing site-specific mutations in double-stranded plasmid DNA which comprises the steps of:
   (a) double digesting a plasmid having a restriction site A, which contains a target sequence, and restriction sites B and C, which flank restriction site A, with restriction endonucleases A and B to produce fragment I and with restriction endonucleases A and C to produce fragment II, wherein restriction endonuclease A produces a 5' overhang;
   (b) denaturating fragments I and II to form a mixture;
   (c) annealing the mixture from step (b) to produce parental homoduplex fragments I and II having a 5'-overhang and a 3'-overhang, heteroduplex fragment III, and heteroduplex fragment IV;
   (d) providing an oligonucleotide primer that can hybridize with the single-stranded region of the heteroduplex fragment IV and that has a sequence that directs mutagenesis;
   (e) extending the 3' ends of heteroduplex fragment IV; and
   (f) ligating heteroduplex fragment IV to produce the double-stranded plasmid DNA mutant.

5. The method according to claim 4, wherein fragment I is dephosphorylated at the 5' terminii prior to step (b).

6. The method according to claim 4, wherein two oligonucleotide primers are ligated to different strands.

* * * * *